United States Patent
Schadewaldt et al.

(10) Patent No.: US 10,223,794 B2
(45) Date of Patent: Mar. 5, 2019

(54) METHOD AND DEVICE FOR GENERATING ONE OR MORE COMPUTER TOMOGRAPHY IMAGES BASED ON MAGNETIC RESONANCE IMAGES WITH THE HELP OF TISSUE CLASS SEPARATION

(71) Applicant: KONINKLIJKE PHILIPS N.V., Eindhoven (NL)

(72) Inventors: Nicole Schadewaldt, Norderstedt (DE); Heinrich Schulz, Hamburg (DE); Michael Guenter Helle, Padenstedt (DE); Steffen Renisch, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 144 days.

(21) Appl. No.: 15/127,426

(22) PCT Filed: Mar. 19, 2015

(86) PCT No.: PCT/EP2015/055738
§ 371 (c)(1),
(2) Date: Sep. 20, 2016

(87) PCT Pub. No.: WO2015/144540
PCT Pub. Date: Oct. 1, 2015

(65) Prior Publication Data
US 2018/0174298 A1 Jun. 21, 2018

(30) Foreign Application Priority Data
Mar. 28, 2014 (EP) ..................................... 14162319

(51) Int. Cl.
*G06F 19/00* (2018.01)
*G06T 7/11* (2017.01)
(Continued)

(52) U.S. Cl.
CPC ................ *G06T 7/11* (2017.01); *A61B 5/055* (2013.01); *A61B 5/7278* (2013.01); *A61B 6/032* (2013.01);
(Continued)

(58) Field of Classification Search
CPC . G06T 7/11; G06T 7/33; G06T 11/008; G06T 2207/10088; G06T 2207/10081;
(Continued)

(56) References Cited

U.S. PATENT DOCUMENTS 8,588,498 B2   4/2013   Novak et al.
8,461,559 B2   6/2013   Lomax
(Continued)

FOREIGN PATENT DOCUMENTS

JP        2011161104 A       8/2011

OTHER PUBLICATIONS

Peter B. Greer, Jason A. Dowling, Jonathan A. Lambert, Jurgen Fripp, . . . , A Magnetic Resonance Imaging-Based Workflow for Planning Radiation Therapy for Prostate Cancer, Feb. 2011, MJA, vol. 194, No. 4, pp. S24-S27.*

(Continued)

*Primary Examiner* — Siamak Harandi

(57) ABSTRACT

A device, system and method for generating one or more simulated CT images from MR images, including retrieving MR image data for one or more body parts of a living being, said MR image data including a plurality of pixels and/or voxels, analyzing said MR image data to identify one or more tissue and/or material types for one or more of said plurality of pixels and/or voxels, registering one or more reference data sets to said identified one or more tissue and/or material types, said reference data sets corresponding to a specific one of said identified tissue and/or material types, said reference data sets including reference values, (Continued)

A

B

C and computing one or more simulated CT images by assigning said reference values to said pixels and/or voxels corresponding to said identified one or more tissue and/or material types.

14 Claims, 3 Drawing Sheets

(51) Int. Cl.
| | |
|---|---|
| G06T 7/33 | (2017.01) |
| G06T 5/00 | (2006.01) |
| G06T 11/00 | (2006.01) |
| A61B 6/03 | (2006.01) |
| A61B 6/00 | (2006.01) |
| A61B 5/055 | (2006.01) |
| G01R 33/48 | (2006.01) |
| G01R 33/56 | (2006.01) |
| A61N 5/10 | (2006.01) |
| A61B 5/00 | (2006.01) |
| G16H 50/50 | (2018.01) |

(52) U.S. Cl.
CPC .......... *A61B 6/505* (2013.01); *A61B 6/5217* (2013.01); *A61N 5/103* (2013.01); *G01R 33/481* (2013.01); *G01R 33/4812* (2013.01); *G01R 33/4828* (2013.01); *G01R 33/5608* (2013.01); *G06F 19/00* (2013.01); *G06T 5/007* (2013.01); *G06T 7/33* (2017.01); *G06T 11/008* (2013.01); *G16H 50/50* (2018.01); *A61N 2005/1055* (2013.01); *G06T 2207/10081* (2013.01); *G06T 2207/10088* (2013.01)

(58) Field of Classification Search
CPC ....... A61B 5/055; A61B 6/5217; A61B 6/505; A61B 6/032; A61B 5/7278; A61N 5/103; G01R 33/5608; G01R 33/4828; G01R 33/481; G01R 33/4812
See application file for complete search history.

(56) References Cited

U.S. PATENT DOCUMENTS

| | | |
|---|---|---|
| 9,299,146 B2 | 3/2016 | Wang |
| 9,342,903 B2 | 5/2016 | Yamaya |

OTHER PUBLICATIONS

Jason A. Dowling, Jonathan Lambert, Joel Parker, Olivier Saldo, . . . , "An Atlas-Based Electron Density Mapping Method for MAgnetic Resonance Imaging (MRI)—Alone Treatment Planning and Adaptive MRI-Based Prostate Radiation Therapy", 2012, Int. J. Oncol. Biol. Phys., vol. 83, No. 1 pp. e5-e11.*

Matthias Hofmann, Ilja Bezrukov, Frederick Mantlik, . . . "MRI-Based Attenuation Correction for Whole-Body PET/MRI: Quantitative Evaluation of Segmentation- and Atlas-Based Methods"; Sep. 2011; Society of Nuclear Medicine, Inc.; vol. 52, No. 9, pp. 1392-1399.*

Dowling, J.A. et al., "An atlas-based electron density mapping method for magnetic resonance imagining (MRI)—Alone treatment planning and adaptive MRI-based prostate radiation therapy". International Journal of Radiation Oncology, May 1, 2012, Abstract.

Greer, P.B., et al., "A magnetic resonance imaging based workflow for planning radiation therapy for prostate cancer", Med J Aust. 2011, Abstract.

Hoffman, M. et al., "MRI-based attenuation correction for whole-body PET/MRI: Quantitative Evaluation of segmentation—and Atlas-Based Methods", Tile Journal of Nuclear Medicine, vol. 52, No. 9 Sep. 1, 2011, Abstract.

Buerger, C. et al., 'Multi-modal vertebra segmentation from MR Dixon for hybrid whole-body PET/MR', In: J. Yao, T. Klinder and S. Li editors. Proceeding of MICCAI 2013 Workshop on Computational Methods and Clinical Applications for Spine Imaging. 2013; Abstract.

Uh, J, et al., "MRI-based treatment planning with pseudo CT generated through atlas registration", Medical Physics, AIP,, vol. 41, No. 5, Jan. 1, 1901, Abstract.

Rank, C.M. et al., "MRI-based treatment plan simulation and adaptation for ion radiotherapy using a classificaiton-based approach" Radiation Oncology, Biomed Central Ltd., vol. 3, No. 1, Mar. 6, 2013, Abstract.

Frantzen-Steneker, M, et al. , In-vivo dosimetric evaluation of an atlas based labeling technique using MR Dixon for MR—only RT treatment planning, Radiotherapy and Oncology 111:S104, Dec. 2014, Abstract.

Helle, M., et al. 'Evaluation of Dixon based Soft Tissue and Bone Classiflcation in the pelvis for MR only based Radiation Therapy Planning ', abstract submitted to ISMRM 2014.

* cited by examiner

METHOD AND DEVICE FOR GENERATING ONE OR MORE COMPUTER TOMOGRAPHY IMAGES BASED ON MAGNETIC RESONANCE IMAGES WITH THE HELP OF TISSUE CLASS SEPARATION

CROSS-REFERENCE TO PRIOR APPLICATIONS

This application is the U.S. National Phase application under 35 U.S.C. § 371 of International Application Serial No. PCT/EP2015/055738, filed on Mar. 19, 2015, which claims the benefit of European Patent Application No. 14162319.9, filed on Mar. 28, 2014. These applications are hereby incorporated by reference herein.

FIELD OF THE INVENTION

The present invention relates to radiation therapy (RT), in particular to a method and device for generating one or more simulated computer tomography (CT) images based on magnetic resonance (MR) images. It finds applications in radiation therapy (RT) treatment and/or planning. In particular, it finds applications in conjunction with magnetic resonance imaging (MRI) techniques. However, it is to be understood that it also finds applications in other fields and is not necessarily limited to the aforementioned applications.

BACKGROUND OF THE INVENTION

In medical imaging, techniques and processes are used to create images of one or more body parts of a living being i.e. anatomical regions, e.g. those of a human body, for clinical purposes and/or medical science. In particular, the internal anatomy of a patient can be imaged to determine how a certain disease has progressed, so that surgical persons are able to distinguish between infected tissues and healthy tissues within the patient. In radiation therapy, such images can be utilized to determine the radiation dose applied to the patient, so that the therapy can be planned such that the amount of radiation the patient receives is minimized while still achieving the goals of therapy.

In general, CT images are used for RT dosimetry. CT images comprising voxel grey values are usually measured in Hounsfield Units (HU), which can be directly translated into electron densities or attenuation coefficients. Hence, the measured HU values can be directly calculated into radiation dosage. However, increasingly often MR images are acquired for diagnostic purposes or organ delineation prior to RT treatment planning. Dose calculation based only on MR images is viewed as being highly beneficial, since this would eliminate the need for generating additional CT images for dose calculations and thus simplifies the workflow and reduce the radiation amount applied to a patient.

To date, there are approaches known from the literature which are used to create estimated density maps or attenuation maps from MR images for RT planning. Due to the physics of the image acquisition, MR intensities do not uniquely correspond to electron densities or attenuation coefficients. Hence, the afore-mentioned maps cannot be derived from the MR images by a simple look-up operation, as is commonly done when deriving these maps from CT images. Solutions proposed so far suffer from a series of shortcomings. For instance, registration of a CT-based density atlas to the MR image may help in regions, where the atlas values are confined and reliable, e.g. the brain. However, in highly variable anatomical regions such as the pelvic region, registration may not be able to cover the anatomical variations between patients, e.g. bladder/bowel filling or movement, resection of structures (e.g. kidneys, liver parts) or pathologic changes.

U.S. Pat. No. 8,588,498 B2 discloses a method for segmenting bones on MR images, including retrieving an MR image and performing an enhancement process on the MR image to generate a bone enhanced MR image. The bone enhanced MR image is then registered to a CT-based bone atlas. An MR image with bone segmentation is generated by segmenting the bone enhanced MR image using the CT-based bone atlas as a mask.

Peter B. Greer et al., "A magnetic resonance imaging-based workflow for planning radiation therapy for prostate cancer", Medical Journal of Australia, 1 Jan. 2011, discloses a method for creating pseudo-CT scan from MRI scan, wherein the method comprises retrieving an MRI scan of a patient, defining prostate and organ contours, registering a CT electron densities atlas to a plurality of tissues by mapping electron densities to the tissues, resulting in a pseudo-CT scan with electron densities mapped to the patient's MRI scan.

JASON A. DOWNLING ET AL., "An Atlas-Based Electron Density Mapping Method for Magnetic Resonance Imaging (MRI)-Alone Treatment Planning and Adaptive MRI-Based Prostate Radiation Therapy", International Journal of Radiation Oncology, 1 May 2012, discloses an automatic method to generate realistic electron density information (pseudo-CT) from MRI scans for prostate radiation therapy.

M. HOFMANN ET AL., "MRI-Based Attenuation Correction for Whole-Body PET/MRI: Quantitative Evaluation of Segmentation- and Atlas-Based Methods", THE JOURNAL OF NUCLEAR MEDICINE, vol. 52, no. 9, 1 Sep. 2011, discloses algorithms for whole-body MRI-based AC (MRAC), including a basic MR image segmentation algorithm and a method based on atlas registration and pattern recognition (AT&PR).

SUMMARY OF THE INVENTION

It is an object of the present invention to provide a method and a device which allows obtaining better simulated CT images from MR images with increased accuracy and reduced amount of work, which can particularly be used in RT treatment and/or planning and/or for dose calculation.

In a first aspect of the present invention a method for generating one or more simulated CT images from MR images is presented comprising retrieving MR image data for one or more body parts of a living being i.e. anatomical regions, the MR image data comprising a plurality of pixels and/or voxels, analyzing the MR image data to identify one or more tissue and/or material types for one or more of the plurality of pixels and/or voxels, registering one or more reference data sets to the identified one or more tissue and/or material types, the reference data sets corresponding to a specific one of the identified tissue and/or material types, the reference data sets comprising reference values, and computing one or more simulated CT images by assigning the reference values to the pixels and/or voxels corresponding to the identified one or more tissue and/or material types, wherein the registering is performed on each of the tissues and/or material types separately.

The present invention thus solves the ambiguity of tissue and patient anatomy based on MR images only, while still location specific density variations as observed in average CT images are taken into account. The present invention thus combines the advantages of both MR and CT imaging techniques. In particular, by utilizing the method according to the present invention, the radiation amount applied to a patient can be reduced compared to methods known from the prior art, where the RT planning is based on real CT images. Simultaneously, by identifying one or more tissue and/or material types in the MR image data, location specific density variations as observed in conventional CT images are taken into account. Another advantage of the present invention resides in the superior sub-tissue contrast of MR images. An example is the treatment of the prostate cancer, where routine MR images are used for a target and risk-structured delineation, while additional CT images are acquired solely for dose computation. Furthermore, additionally acquired CT images can be avoided and the problems connected to the CT-MR registration can also be reduced. The usage of tissue and/or material type specific reference data sets increases the reliability of the assignment of reference values even for body parts with highly variable anatomy, such as the pelvis.

The method according to the afore-mentioned prior art (U.S. Pat. No. 8,588,598 B2) is afflicted with several disadvantages. According to the method disclosed therein, MR images with bone segmentation are created for RT treatment and/or planning, wherein this bone segmentation is done analyzing MR signal intensity and then using a bone atlas as a mask to remove artifacts from this method. Such a method relies on the fact, that assigning an average attenuation value per tissue class is sufficient, ignoring regional variations as long as they are within a given tissue class. In contrast, the method of the present invention generates simulated CT images, which re-present typical local variations in the attenuation, while still using the MR-information available, e.g. a tissue-class separation.

In a preferable embodiment, the one or more reference data sets comprise a CT-based atlas, the reference values comprising Hounsfield Unit (HU) values.

Advantageously, the simulated CT images are generated by not only assigning one value per tissue class, but deriving real CT values from a tissue class specific CT-value atlas. In a more specific embodiment, the atlas consists of CT value predictions for each of the one or more tissue and/or material types to be identified in the MR image. CT-based atlases with HU values known as CT-based HU atlases can be generated after the one or more tissue and/or material types have been separated in CT images from a database. This atlas generation is a preparation step, which does not require knowledge of the patient from which the MR is taken and may be performed long before. In one embodiment, atlas generation is performed for each of the tissue classes and/or material types by registering the separated HU value information specific for this tissue class from each of the training CT images to a common reference frame. This enables calculation of average HU values within the pixels and/or voxels of the same tissue and/or material type. Such an average HU value is reliable, since it is calculated in a homogeneous setting.

For a patient MR a simulated CT image is then assembled by separating the same tissue and/or material classes represented in the reference data or atlas. For each of those classes the corresponding specific reference data or atlas can be registered and the HU values assigned to the MR voxels. In a preferred embodiment, the registration is done specifically for each class, such that it is reliable, even in the context of highly varying anatomical neighborhood.

With this method the class-separation information from the MR image and the HU value information from class specific reference data are merged. After this, the correlation between HU values and radiation density and/or attenuation coefficients is straightforward, which enables easy generation of attenuation and/or density maps.

In another preferable embodiment, the CT-based atlases are averaged from a plurality of CT images. This increases the reliability of the CT-based atlases.

In another preferable embodiment, the CT-based atlases are location specific and/or tissue and/or material type specific. This is advantageous since the reliability of the CT-based atlases and consequently the simulated CT images can be increased. Preferably, this is realized by utilizing the one or more tissue and/or material types that are location and patient specific, which is straightforward after being derived from the MR image data of the patient. However, since they reflect a pool of patients, the same location may hold HU values for each of the tissue and/or material types, whereas those HU values are specific to the tissue and/or material type. Different structures may be present in the same location of different patients, so that even a perfect atlas registration alone, which is prior art, may not be sufficient for accurate and secure RT planning With this combination of location and patient specific tissue and/or material types and location and tissue and/or material type specific HU values, however, the assignment of HU values is reliable even for highly variable anatomy.

Registration is used both for generating the simulated CT from an MR based on tissue type specific references, and in a previously described embodiment for generating the tissue type specific references as atlases. In one preferable embodiment, the registering comprises applying at least one rigid registration and/or at least one non-rigid, in particular deformable, registration. The rigid registration translates and rotates the reference data set, in particular the CT-based atlases, to the retrieved MR image data. The non-rigid, in particular deformable, registration is used to account for variations in anatomies, so that for instance significant non-linear motion between two image acquisitions produced by inherent differences on the retrieved MR images can be recovered.

In another preferable embodiment, the registration is performed on each of the tissue and/or material types separately. With this method, the registration is likely to be more accurate within the tissue and/or material type currently considered and the assignment of HU values to MR voxels to produce a simulated CT is more reliable.

In another preferable embodiment, the tissue and/or material types are mutually disjoint. This is for instance the case, when any anatomical tissue can be assigned uniquely to at most one of the tissue and/or material types.

In another preferable embodiment, the assignment to tissue and/or material types from the MR image is mutually disjoint. This is for instance the case, when one voxel of the MR image data will not be assigned two or more tissue and/or material types. This is for instance also the case, when the tissue and/or material types are mutually disjoint and each voxel belongs to exactly one type. In this way, the registering of reference data sets, in particular CT-based atlases for each tissue and/or material type is particularly easy, since for instance intermediate values can be attributed to the variability of adjacent tissue and/or material types.

In another preferable embodiment, the tissue and/or material types are not disjoint and each anatomical tissue and/or each MR voxel can be assigned to more than one tissue and/or material type. Since the assignment of HU values based on reference data is tissue and/or material specific, this may result in more than one HU value being assigned to one MR voxel. In one preferable embodiment, this assignment may be interpolated to obtain one HU value for the one MR voxel. This is anatomically advantageous, since the MR voxel may contain parts of both tissue types and the simulated CT image may show an intermediate HU value to the HU values of each tissue type.

In another preferable embodiment, the analyzing of the MR image comprises segmenting and/or reconstructing and/or applying a body extraction algorithm and/or a method involving the DIXON reconstruction of the inphase images of the MR acquisition values to MR image data. In this way, the retrieved MR image data can be separated into different tissue and/or material types particularly efficiently and reliably. Different tissue and/or material types have different requirements in their separation, so that the present invention enables an optimization of analyzing the retrieved MR image data.

In another preferable embodiment, the MR image data comprise pelvic MR image data, the one or more tissue and/or material types comprising air, fat, water, bone marrow and/or cortical bone. The pelvic region belongs to the highly variable anatomical regions of the human body, where registration of the reference data sets, in particular the CT-based atlases to the retrieved MR image data is known to be difficult. It is, for instance, not straightforward if possible at all to cover the anatomical variations between patients or between different scans of the same patient, e.g. the filling of the bladder or the current positioning of the intestines. The present invention, in contrast, enables reliable registration only of the tissue and/or material type to the corresponding specific reference data sets, in particular CT-based atlases. The assignment of reference values, in particular HU values, to the one or more pixels and/or voxels in the retrieved MR image data is thus more reliable, as both the registration is better and the assignment of HU values is performed tissue class specific. As a result, easy and reliable RT planning is possible using the simulated CT images generated according to the present invention.

In another aspect of the invention, a device for generating one or more simulated CT images from MR images is presented comprising a data retriever for retrieving MR image data for one or more body parts of a living being i.e. anatomical regions, such as those of a patient, the MR image data comprising a plurality of pixels and/or voxels, an analyzing unit for analyzing the MR image data to identify one or more tissue and/or material types for one or more of the plurality of pixels and/or voxels, a registering unit for registering one or more reference data sets to the identified one or more tissue and/or material types, the reference data sets corresponding to a specific one of the identified tissue and/or material types, the reference data sets each comprising reference values, and a processing unit for computing one or more simulated CT images by assigning the reference values to the pixels and/or voxels corresponding to the identified one or more tissue and/or material types, wherein the registering is performed on each of the tissues and/or material types separately.

In a further aspect of the present invention, a system for radiation therapy treatment and/or planning is presented comprising a device as disclosed herein for generating one or more simulated CT images from MR images and a planning unit configured to set up an radiation therapy plan by generating dosimetry program based on the generated one or more simulated CT images.

Advantageously, the system according to the present invention enables reliable and easy RT treatment and/or planning, since it combines the advantages of using MR images and prior information from CT images of different patients. In particular, it exploits the advantage of the direct correlation between the HU values of CT images and attenuation coefficients and/or radiation densities of dosimetry programs. Simultaneously, it takes into account the variability of anatomical structures, for instance between patients and/or between locations.

In a preferable embodiment, the system further comprises an MR imaging (MRI) unit configured to generated MR image data for one or more body parts of a living being i.e. anatomical regions, such as those of a patient. This embodiment has the advantage that it enables the system which generates MR image data and simulated CT images based on the MR image data simultaneously. Furthermore, such a system is able to independently assist surgical persons such as a radiologist, in RT treatment and/or planning Such a system can also be used to realize integrated MR-Linac and/or PET/MR systems where attenuation and/or radiation maps can be generated and the corresponding therapy can be conducted accordingly. Preferably, the dosimetry programs comprise an attenuation and/or density map, which enables easy RT treatment and/or planning since such a map provides the user with a direct instruction of dosimetry which may be configured individually for each patient.

In yet a further aspect of the invention, a computer program is presented comprising program code means for causing a computer to carry out the steps of the method disclosed herein when the computer program is carried on a computer.

Preferred embodiments of the invention are defined in the dependent claims. It shall be understood that the claimed device, system, medium and computer program have similar and/or identical preferred embodiments as the claimed method and as defined in the dependent claims.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
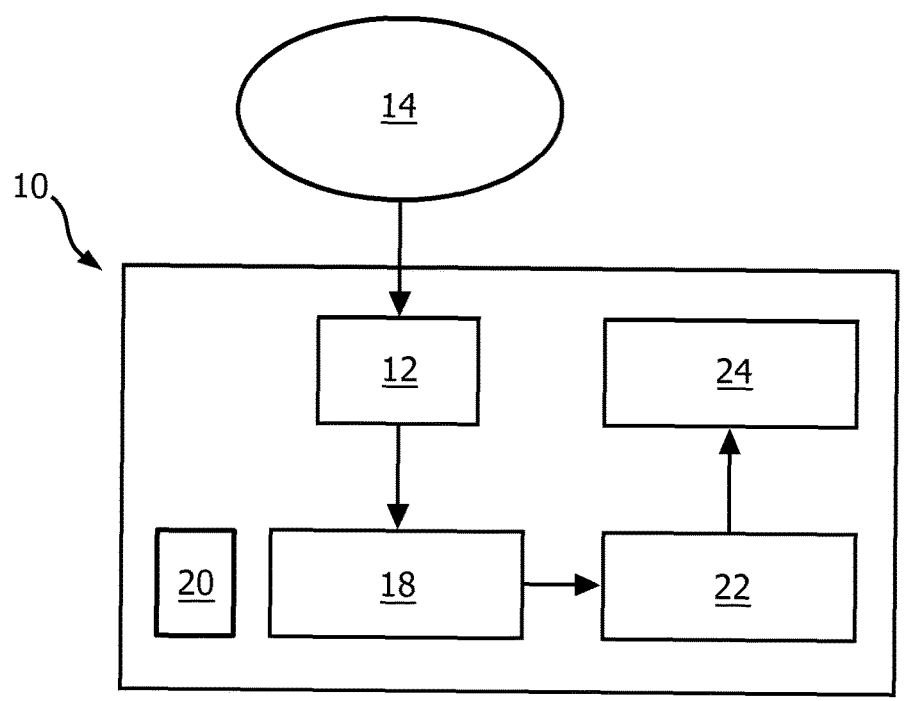
FIG. 1 shows a schematic block diagram of a device for generating one or more simulated CT images from MR images in accordance with an embodiment.

With reference to FIG. 1, a schematic block diagram of a device 10 for generating one or more simulated CT images from MR images in accordance with an embodiment is shown. The device 10 comprises a data retriever 12 configured to receive MR image data 14 for one or more body parts of a living being i.e. anatomical regions, such as those a human, a mammal or a bird. The data retriever 12 may comprise one or more data input interfaces 16 (not shown) for receiving the MR image data 14 from one or more external databases, including hospital intranets, internet and other communication networks, as well as personal computers, mobile devices, cloud systems. The one or more data input interfaces 16 may comprise a direct wired link or a fiber optic connection or wireless communication link or the like. The MR image data comprise a plurality of pixels and/or voxels and can be generated by a magnetic resonance imaging (MRI) unit. Alternatively, the MR image data may be generated by computer simulation. The MR image data are preferably spatially encoded, whereby a 2D and/or 3D spatial decoding may be possible. The MR image data preferably comprise parameters such as intensity and/or magnitude and/or phase and/or relaxation time and/or magnetization transfer and/the like, from which one or more may be ascertained. Further preferably, one or more of the afore-mentioned parameters may comprise a real and/or an imaginary part which can be used to derive phase and/or magnitude information. The MR image data may correspond to one or more images of one or more body parts of one or more living beings i.e. anatomical regions, such as those of patients. The one or more body parts i.e. anatomical regions may include the head, the brain, the pelvic region, the bladder, the bowels, the kidneys, the liver parts and other known body parts of the human body or an animal body.

The device 10 further comprises an analyzing unit 18 configured to analyze the MR image data 14 to identify one or more tissue and/or material types for one or more of the plurality of pixels and/or voxels. The one or more tissue and/or material types may include water tissue, fat tissue, air tissue, bone tissue and other tissues and/or materials known in the field of medical imaging and/or anatomy. In particular, the bone tissues may include bone marrow tissues, cortical bone tissues and other bone tissues known in the field of medical imaging and/or anatomy. The analyzing unit 18 may use segmentation, reconstruction, body extraction algorithms, the DIXON reconstruction of the inphase images of the MR acquisition methods and other methods known in the field of medical imaging to identify tissue and/or material types. Further, the analyzing unit 18 may analyze phase and/or intensity and/or other parameters contained in the MR image data, such as T1, T2, T2*, Te. In a preferable embodiment, the analyzing unit 18 derives the water tissue and the fat tissue via a Dixon reconstruction while it may derive the air tissue using a body extraction algorithm. The bone tissues may be segmented with a model-based approach as published in Christian Buerger, Jochen Peters, et al., Multi-model vertebra segmentation from MR Dixon for hybrid whole-body PET/MR, proceeding of MICCAI 2013 workshop on computational methods and clinical applications for spine imaging, 2013, pp 144-155. Within the bone tissues, a separation of cortical bone tissues and bone marrow tissues may be realized based on the DIXON reconstruction of the inphase images of the MR acquisition with a noise threshold.

In another preferable embodiment, the analyzing unit 18 may identify one or more tissue and/or material types for a single pixel and/or a single voxel of the MR image data 14. Each single pixel and/or each single voxel may be analyzed to determine one or more tissue and/or material types that can and/or cannot be contained therein, or a probability that each pixel and/or each voxel contains each of two or more tissue and/or material types. Preferably, the analyzing unit 18 is configured to access one or more MR image data sets for differentiating between different tissue and/or material types. The one or more MR image data sets may be stored in a memory unit 20, which may be integrated in the device 10 or arranged externally of the device 10. The memory unit 20 may be connected to the analyzing unit 18 via a communication link known in the art.

The device 10 comprises a registering unit 22 configured to register one or more reference data sets to the MR image data 14 after being retrieved by the data retriever 12. The one or more reference data sets comprise each reference values, which can be assigned to the MR image data 14. In particular, the reference values can be assigned to the one or more pixels and/or voxels of the MR image data 14 after being retrieved. Each of the reference data sets is specific for a different one of the tissue and/or material types identified by the analyzing unit 18. For instance, one reference data set may be specific for a bone tissue whereas another reference data set may be specific for fat tissue. In a preferable embodiment, the one or more reference data sets each comprise a CT-based atlas. The atlas may contain a reference image in which structures of interest have been segmented. The segmentation can be carried out by hand or by computer. The atlas may also contain location specific average CT values based on the tissue type of interest only.

A CT-based atlas is an atlas which is generated from one or more CT images. The procedure of generating such a CT-based atlas is described in detail with reference to FIG. 4. Preferably, the registering unit 22 is configured to retrieve the one or more reference data sets from a memory unit, further preferably the memory unit 20. In a preferable embodiment, the registering unit 22 is connected to the memory unit 20 via a communication link known in the art. In a preferable embodiment, the reference values of the one or more CT-based atlases comprise Hounsfield Unit (HU) values. The HU values are values according to the HU scale which is the linear transformation of the original linear attenuation coefficient measurement into one in which the radial density of distilled water at the standard pressure and temperature (STP) is defined as 0 HU, while the radial density of air at STP is defined as −1000 HU. Hence, such CT-based atlases can be utilized for RT planning.

In order to register the CT-based atlases to the MR image data 14, the registering unit 22 preferably applies a rigid registration or a non-rigid registration or both. During a rigid registration, a CT-based atlas for specific tissue and/or material type, for instance a CT-based bone atlas may be translated and/or rotated to an MR image, the MR image corresponding to the MR image data 14 retrieved by the data retriever 12. In one embodiment, the rigid registration uses Mattes Mutual Information (MMI) as a metric and Regular Step Radiant Descent (RSRD) as an optimizer. In another embodiment, the registering unit 22 captures the difference in positions between the CT-based atlas and the MR image by applying affine registration. A non-rigid registration is utilized to compensate the normal anatomical variability between the CT-based atlas and the MR image. In a preferable embodiment, the registering unit 22 utilizes a deformable registration based on extracted surfaces (rigid registration based on the body outline or the extracted bones). Further preferably, the registering unit 22 is configured to apply different registrations to each of the tissue and/or material types. In another embodiment, the registration considers only the tissue and/or material type of interest to compute an optimal rigid or non-rigid registration to the reference data set for this tissue and/or material type. For instance, for bone tissues a deformable registration based on the extracted surfaces may be utilized, while for the other tissues such as air, fat and water, a rigid registration based on the body outline or the extracted bones or mutual information on one of the MR images may be utilized.

The device 10 further comprises a processing unit 24 configured to compute one or more simulated computer tomography (CT) images. The processing unit 22 may comprise any processor known in the art, which is configured to assign the reference values to the plurality of pixels and/or voxels of the MR image data 14 in accordance with the identified tissue and/or material types. In a preferable embodiment, the processing unit 24 is configured to assign location-specific HU values to a plurality of voxels where a bone tissue type has been identified by the analyzing unit 18. Preferably, the processing unit 24 is connected to a displaying unit 26 (not shown), which is configured to display the one or more simulated CT images computed by the processing unit 24. The displaying unit 26 may be integrated into the device 10 or be configured as a separate unit, for instance a displaying unit embedded into a mobile communication device such as a smartphone.

Figure 2:
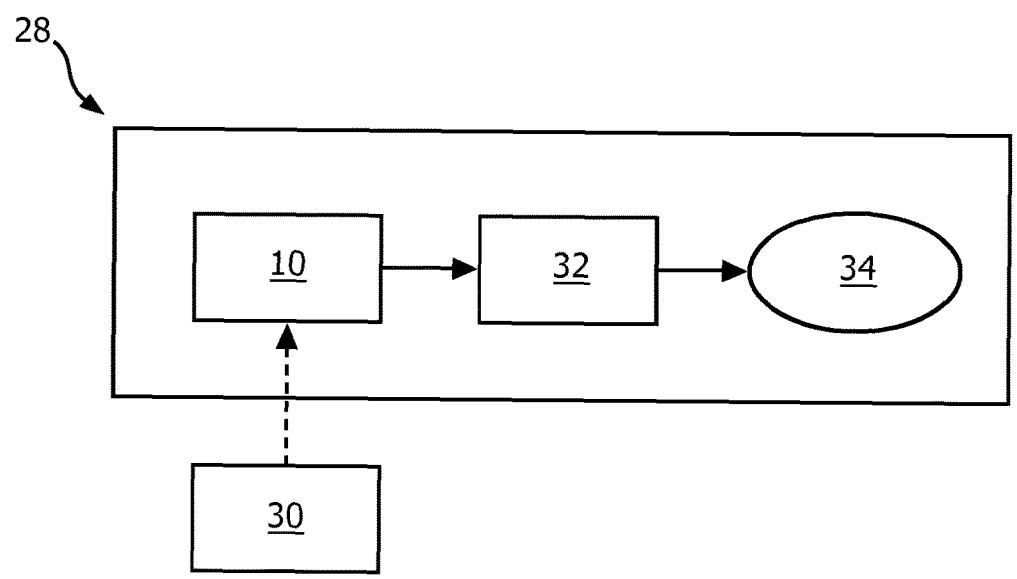
FIG. 2 shows a schematic block diagram of a system for radiation therapy (RT) treatment and/or planning in accordance with an embodiment.

With reference to FIG. 2, a schematic block diagram of a system 28 for radiation therapy (RT) treatment and/or planning in accordance with an embodiment is shown. The system 28 comprises a device for generating one or more simulated CT images from MR images, preferably the device 10 shown in FIG. 1. The device 10 retrieves MR image data 14 from an MR imaging (MRI) unit 30, which is preferably integrated into the system 28. Alternatively, the MRI unit 30 may be an external MRI unit connected to the system 28 and/or the device 10 via a communication link known in the art. Further alternatively, the device 10 retrieves MR image data 14 from a memory unit, in particular the afore-mentioned memory unit 20 cooperating with the device 10 as elaborated with reference to FIG. 1. The system 28 comprises further a planning unit 32, which is configured to set up an RT plan by generating a dosimetry program 34 based on the generated one or more simulated CT images. The dosimetry program 34 may comprise one or more attenuation and/or density maps used for correcting dose calculation.

The system 28 may be any imaging system applicable for RT treatment and/or planning, in particular based only on MR images. Possible examples include without being restricted to a CT imaging system, an MRI system, an X-ray imaging system, or nuclear medicine imaging system such as position emission tomography (PET) and single proton emission computer tomography (SPECT). A combined CT-MR or PET-MR or SPECT-MR or X-ray-MR system may also be envisaged. The system 28 may comprise any additional components which are known to be used in conjunction with one or more of the afore-mentioned examples, such as a remote or wired operator console.

Figure 3:
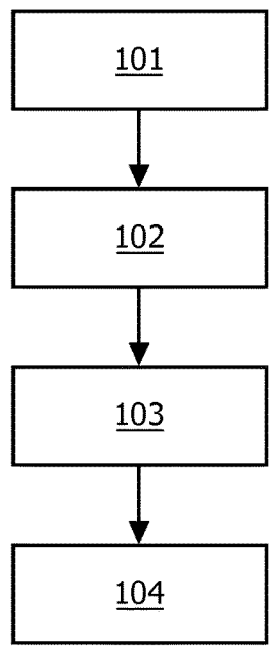
FIG. 3 shows a method for generating one or more medical images based on MR in accordance with an embodiment.

With reference to FIG. 3, a schematic block diagram of a method for generating one or more medical images based on MR images in accordance with an embodiment is shown.

In step 101, MR image data 14 comprising a plurality of pixels and/or voxels are retrieved by the data retriever 12. The MR image data 14 may correspond to one single MR image or a series of MR images. The MR image data 14 may preferably correspond to an MR image of a human body.

In step 102, the MR image data 14 are analyzed by the analyzing unit 18 in order to identify one or more tissue and/or material types for one or more of the plurality of pixels and/or voxels. In a preferable embodiment, the tissue types water, fat, air, bone marrow and/or cortical bone may be identified for one or more of the plurality of voxels by the analyzing unit 18. In another preferable embodiment, the tissue types water and fat are identified and separated for a plurality of voxels in the MR image data 14 by Dixon reconstruction. In a further preferable embodiment, a plurality of tissue types are separated by segmenting the MR image corresponding to the MR image data 14. In another preferable embodiment, the step 102 further comprises a separation of cortical bone and bone marrow tissue types based on the DIXON reconstruction of the inphase images of the MR acquisition and a noise threshold.

In step 103, one or more reference data sets are registered by the registering unit 22. In a preferable embodiment, the reference data sets are CT based HU value atlases for each of the tissue and/or material types of interest. In another preferable embodiment, a CT-based atlas is registered to at least one section of the MR image data 14, wherein the at least one section corresponds to a plurality of voxels where a bone tissue type has been identified by the analyzing unit 18. The CT-based atlas corresponds to the identified bone tissue type. In another preferable embodiment, a plurality of CT-based atlases correspond each to a different one of the tissue types air, fat, water, bone marrow and cortical bone. In a preferable embodiment, the step 103 comprises the application of a rigid registration or a non-rigid registration or both, wherein the registration may be different for each tissue type. For instance, for bone tissue types a deformable registration based on the extracted surfaces may be utilized, while for other tissue types a rigid registration based on the body outline or the extracted bones or on mutual information between the MR image and reference CT image may be utilized. In another preferred embodiment the registration is based the plurality tissue types separated previously and an atlas of tissue type prevalence.

In step 104, one or more simulated computer tomography (CT) images are computed by assigning the reference values to the pixels and/or voxels according to the identified tissue and/or material types. In a preferable embodiment, location-specific HU values may be assigned to a plurality of voxels of the MR image data 14, where a bone tissue type has been identified by the analyzing unit 18. In another preferable embodiment, location-specific HU values of a plurality of CT-based atlases are assigned to a plurality of voxels of the MR image data 14 according to the tissue and/or material types identified in the voxels.

Figure 4:
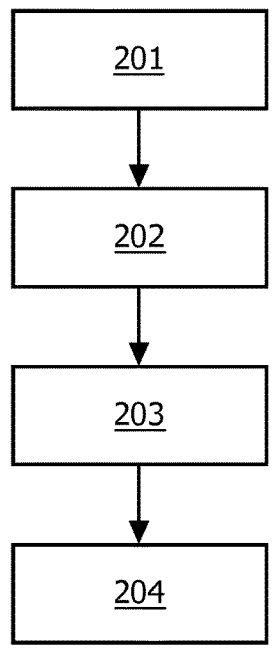
FIG. 4 shows a method for generating a CT-based atlas in accordance with an embodiment.

With reference to FIG. 4 a schematic block diagram of a method for generating a CT-based atlas in accordance with an embodiment is shown.

In step 201, a plurality of CT images are retrieved. The CT images may be generated by a CT imaging unit, which may preferably be cooperating with the device 10 or connected thereto via a communication link known in the art. Alternatively, the CT images may be generated by computer simulation. The CT images may further preferably be generated for one or more body parts of a living being i.e. anatomical regions, such as a those of patient. For instance, the CT images may contain those for the pelvic region of the human body.

In step 202, one or more tissue and/or material types are derived from the plurality of CT images. In a preferable embodiment, one or more of the tissue types water, fat, air, bone marrow and cortical bone are derived from the plurality of CT images, e.g. for the pelvic region of a patient. The afore-mentioned tissue types can be estimated by using overlapping gray value ranges, such that intermediate values are attributed to the variability of two adjacent tissue types. Subsequent image processing may be used to remove unlikely voxels from the tissue fraction. In a further preferable embodiment, location specific tissue and/or material types corresponding to specific structures of one or more body parts i.e. anatomical regions may be derived by segmenting a plurality of CT images.

In step 203, the one or more tissue and/or material types derived from the plurality of CT images are registered onto each other. In a preferable embodiment, the step 203 involves a rigid registration and/or a non-rigid registration. The different registrations may be applied to different tissue and/or material types, depending on their specific anatomic properties such as location and/or patient variability, material composition and compatibility.

In step 204, from the plurality of HU values for a specific tissue and/or material type derived from the plurality of CT images atlas HU values and/or other atlas values are generated. In a preferable embodiment, the step 204 comprises averaging the HU values for each location over all HU values from a given tissue type at that location. In a further preferable embodiment, the specific tissue and/or material type comprises a bone tissue type which has been derived in step 202 by taking a section of the plurality of pixels from the plurality of CT images corresponding to a bone into account. In a preferable embodiment, at least one of the steps illustrated in FIG. 4 may be carried out by or in conjunction with the device 10 in FIG. 1.

Figure 5:
FIG. 5A shows an MR image.
FIG. 5B shows a simulated CT image using a method in accordance with an embodiment.
FIG. 5C shows a CT image generated directly from CT imaging.

With reference to FIG. 5A-C, an MR image generated by MR imaging, a simulated CT image generated in accordance with an embodiment as well as a CT image generated by CT imaging, respectively, are shown for the femur head region.

In FIG. 5A, an MR in-phase image is exemplarily shown for the femur head region including the rectum. The MR in-phase image is generated by MR imaging. MR in-phase images are superior in terms of Signal Noise Ratio (SNR) compared to MR intensity images, leading to improved image contrast for tissue and/or material types where low signal intensity is expected. In FIG. 5B, a simulated CT image generated based on the MR in-phase image in FIG. 5A is shown. A plurality of tissue types including water, fat and bone have been derived from the MR in-phase image prior to generating the simulated CT image. Bone intensity variations are modeled by a CT-based atlas, while water and fat parts are deduced from the DIXON reconstruction of the MR acquisition. FIG. 5C shows a CT image generated by CT imaging for the same region shown in FIG. 5A-B. The close comparability between the simulated and the "real" CT images in FIG. 5B and FIG. 5C indicates the obvious advantage of applying a tissue-specific CT-based atlas for generating simulated CT images based on MR images.

The device 10 and/or the system 28 may preferably be used in conjunction with one or more non-transitory computer-readable media carrying software which controls one or more devices and/or systems to perform the method described with reference to FIG. 3 and/or FIG. 4. The computer-readable media may include volatile and non-volatile, removable and non-removable media implemented in any method or technology for storage of information such as computer-readable instructions, data structures, program modules or other data forms. Computer-readable media further include, but are not limited to, random access memory (RAM), read-only memory (ROM), phase change memory (PCM), flash memory, magnetic memory and other memory forms. The computer-readable media are further preferably accessible by internet, intranet, cloud systems and other communication systems known in the art.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A method for generating one or more simulated CT images from MR images, comprising acts of:
   retrieving MR image data representative of one or more anatomical regions, said MR image data comprising a plurality of pixels and/or voxels;
   analyzing said MR image data to identify a plurality of tissue and/or material types for one or more of said plurality of pixels and/or voxels;
   registering a corresponding tissue and/or material type-specific CT-based atlas comprising Hounsfield Unit (HU) values to each of said identified plurality of tissue and/or material types; and
   computing one or more simulated CT images by assigning said Hounsfield Unit (HU) values to said pixels and/or voxels corresponding to said identified plurality of tissue and/or material types,
   wherein each tissue and/or material type-specific CT-based atlas corresponds to a specific one of said identified tissue and/or material types,
   and wherein said registering is performed on each of the tissue and/or material types separately.

2. The method according to claim 1, wherein said CT-based atlases are averaged from the plurality of CT images.

3. The method according to claim 1, wherein said CT-based atlases are location specific.

4. The method according to claim 1, wherein said registering comprises applying at least one rigid registration and/or at least one non-rigid deformable, registration.

5. The method according to claim 1, wherein said tissue and/or material types are mutually disjoint.

6. The method according to claim 1, wherein said assigning to said identified tissue and/or material types from the MR image is mutually disjoint.

7. The method according to claim 1, wherein said analyzing comprises segmenting and/or reconstructing and/or applying a body extraction algorithm and/or a method involving the DIXON reconstruction of the inphase images of the MR acquisition to MR image data.

8. The method according to claim 1, wherein said MR image data comprise pelvic MR image data, said plurality of tissue and/or material types comprising air, fat, water, bone marrow and/or cortical bone.

9. A device for generating one or more simulated CT images from MR images, comprising:
a processor
configured to retrieve MR image data representative of one or more anatomical regions, said MR image data comprising a plurality of pixels and/or voxels;
configured to analyze said MR image data to identify a plurality of tissue and/or material types for one or more of said plurality of pixels and/or voxels,
configured to register a corresponding tissue and/or material type-specific CT-based atlas comprising Hounsfield Unit (HU) values to each of said identified plurality of tissue and/or material types; and
configured to compute one or more simulated CT images by assigning said Hounsfield Unit (HU) values to said pixels and/or voxels corresponding to said identified plurality of tissue and/or material types,
wherein each tissue and/or material type-specific CT-based atlas corresponds to a specific one of said identified tissue and/or material types,
and wherein said registering is performed on each of the tissue and/or material types separately.

10. A system for radiation therapy treatment and/or planning, comprising:
a device as claimed in claim 9 configured to generate one or more simulated CT images from MR images, wherein the processor is further configured to set up a radiation therapy plan by generating a dosimetry program based on said generated one or more simulated CT images.

11. The system according to claim 10, further comprising a magnetic resonance imaging (MRI) device configured to generate MR image data representative of one or more anatomical regions.

12. The system according to claim 10, wherein said dosimetry program comprises an attenuation and/or density map.

13. A computer program stored on tangible computer-readable storage-memory, the computer program comprising program code configured to cause a computer to carry out the acts of the method as claimed in claim 1 when said computer program is carried out on a computer.

14. The method according to claim 1, wherein the anatomical regions are body parts of a living being.

* * * * *